United States Patent [19]
Warner

[11] Patent Number: 5,542,826
[45] Date of Patent: Aug. 6, 1996

[54] FLUID DELIVERY SYSTEM WITH MOUNTING LINKAGE

[75] Inventor: Eric A. Warner, Vista, Calif.

[73] Assignee: IVAC Corporation, San Diego, Calif.

[21] Appl. No.: 304,729

[22] Filed: Sep. 12, 1994

[51] Int. Cl.$^6$ .................................................. F04B 43/12
[52] U.S. Cl. .......................................... 417/474; 604/153
[58] Field of Search ........................ 417/474, 477.1, 417/477.2, 63; 604/153; 73/19.1, 756, 753, 754; 128/DIG. 12

[56] References Cited

U.S. PATENT DOCUMENTS

| | | | |
|---|---|---|---|
| 1,158,228 | 10/1915 | Kaskie . | |
| 4,728,265 | 3/1988 | Cannon | 417/363 |
| 4,954,046 | 9/1990 | Irvin et al. | 417/53 |

Primary Examiner—Charles Freay
Attorney, Agent, or Firm—Fuldwider Patton Lee & Utecht

[57] ABSTRACT

A fluid delivery system in which the pressure platen for a fluid conduit is fixedly mounted to the pump and the pumping mechanism is movable in relation to the platen to control the force exerted on the conduit. A mounting system comprising a four-bar linkage retains the movable pumping mechanism in a predetermined orientation to the conduit through the mechanism's range of movement. The pumping mechanism is spring loaded towards the conduit. The peristaltic fingers of the pump mechanism are located in guides with the drive means for those fingers rigidly mounted to that guide. Should the movements of one or more fingers through the respective guide be prevented, the drive means will be stopped from movement and the pumping mechanism will stall rather than back off and allow free flow.

23 Claims, 7 Drawing Sheets

FLUID DELIVERY SYSTEM WITH MOUNTING LINKAGE

BACKGROUND

The invention generally relates to fluid delivery systems used to infuse parenteral fluids to patients intravenously and more particularly, to a mounting linkage for mounting a pumping mechanism.

Physicians and other medical personnel apply fluid infusion therapy to treat various medical complications in patients. For safety reasons and in order to achieve optimal results, it is desirable to infuse parenteral fluid in accurate amounts as prescribed by the physician and in a controlled fashion.

Over the years, various devices and methods have been developed to improve the infusion of fluids in a controlled and more accurate fashion. One type of infusion device is a peristaltic pump that acts on a portion of the tube carrying fluid between the fluid reservoir and the patient. More specifically, a linear-type peristaltic pump sequentially occludes adjacent segments of flexible tubing in a wave-like fashion to create a moving zone of occlusion and force fluid through the tubing. Operation of such a pump typically involves the mechanical operation of a peristaltic pumping mechanism on a flexible tubing positioned between the pumping mechanism and a platen or rigid base and a drive mechanism for driving the pumping mechanism. The pumping mechanism typically comprises a series of pumping devices (fingers) that are driven by a series of drive cams that are mounted on a rotating cam shaft, the cam shaft being coupled to a drive mechanism such as a step-motor. The pumping devices are received in a guide device that confines the movement of the pumping devices to a linear movement against the tubing. The speed of the drive mechanism may be adjusted to achieve a desired volumetric flow rate.

A force limited type of peristaltic pump has a biasing means such as a spring for limiting the force exerted by the pumping devices on the tubing. The pumping devices of a linear peristaltic pump move the same amount in their reciprocal, linear pumping action. The spring permits relative motion between the tubing and the pumping devices so that the force the pumping devices are able to exert on the tubing is kept at a predetermined maximum, which is proportional to the spring force. In one configuration, the pumping mechanism is held in a fixed position and the tubing is placed between the mechanism and a rigid platen, the platen being biased by a spring or springs towards the pumping mechanism. The tubing is placed between the platen and the pumping mechanism. If the compressive force supplied by the moving pumping devices against the tubing exceeds a predetermined threshold established by the springs, the springs yield and allow the platen to be displaced in the direction of such compressive force ensuring that the compressive force remains at the predetermined constant.

The above spring-biased platen approach is not practical in the case where a pumping segment is used that has its own built in platen already coupled to a fluid conduit segment for receiving the pumping devices, and the segment is rigidly mounted in an external position on the pump. In such a case, the pumping devices may be biased towards the tubing so that they may move away from the tubing and platen if the force they exert should exceed the maximum.

However, an important consideration in the mounting of the peristaltic pumping devices, the platen, and the biasing means is keeping a predetermined orientation between the devices when they must move relative to each other to limit the force applied to the tubing. For example, the peristaltic fingers of a linear peristaltic pump are typically mounted in a perpendicular orientation to the tubing to be operated upon and the platen. The platen is typically parallel to the tubing. In the case where the spring-loaded platen must move to relieve the force applied by the fingers, it should do so while remaining parallel to the tubing and perpendicular to the fingers. Likewise in the case where the peristaltic fingers are spring-loaded and must retract from the tubing, they should do so while remaining perpendicular to that tubing so that the correct pumping action continues to occur.

A further consideration in the design of a force limited system is immunity to agents that may interfere with the proper functioning of the force limiting mechanism. In the case where parenteral or other fluids may enter the spaces between the peristaltic fingers or their guides, this fluid may bind the fingers together or to their guides and prevent them from properly moving through the guides. If the mechanism is constructed so that the mechanism can still function partially, it may lift off of the tubing and a free flow condition may result. Such a condition is not desirable. Consequently, it is desirable that the peristaltic pump include a mechanism that prevents unregulated free flow of parenteral fluid from being introduced to the patient.

Hence, those skilled in the art have recognized the need for a mounting mechanism or linkage for use with a peristaltic-type infusion pump that maintains a predetermined orientation between the pumping devices, the tubing and the platen during the times when relative motion occurs between them in force limiting and other operational situations. In addition, those skilled in the art have also recognized the need for a mounting linkage that also prevents free flow through the pumping segment conduit in the event that an outside agent interferes with the proper motion of the pumping devices against the conduit. The present invention fulfills these and other needs.

SUMMARY OF THE INVENTION

Briefly, and in general terms, the present invention is directed to a system for delivering fluid to a patient, the system including a linkage for mounting a pumping mechanism in a predetermined orientation to a fluid conduit and maintaining that orientation through relative movement between the pumping mechanism and the conduit. In a further aspect, the system is also for preventing free flow of fluid through the conduit in the event that the pumping mechanism becomes unable to continue in its pumping motion.

More particularly, the system for delivering fluid to a patient includes a rigid base mounted so as to position the fluid conduit between the rigid base and the pumping mechanism. The pumping mechanism has a plurality of movable pumping devices guided by a guide device to control the direction of movement of the pumping devices. The pumping mechanism further includes a drive means rigidly mounted to the guide device and operative on the pumping devices to move the pumping devices in the guide device through a predetermined range of motion.

The mounting linkage is configured to mount the pumping mechanism in a predetermined orientation relative to the rigid base and in relation to the fluid conduit so that the pumping devices move into and out of contact with the fluid conduit for moving fluid through the conduit. The mounting linkage allows movement of the pumping mechanism relative to the rigid base, but constrains such movement to the predetermined orientation.

In a more particular aspect of the invention, the mounting linkage has a plurality of links pivotally interconnected wherein one of such links, defined as a base link, is fixed in relationship to the rigid base and about which the pumping mechanism moves.

In a further aspect of the invention, the pumping mechanism forms one of the links to define a pumping mechanism link, the pumping mechanism link connected by at least one additional link to the base link.

In a particular aspect of the invention, the mounting linkage comprises a four-bar linkage, one of such links being the base link and another of such links being the pumping mechanism link.

In yet a further aspect of the invention, the four bar linkage mechanism is shaped as a parallelogram with opposing links having the same length and always being parallel to each other.

In a more particular aspect of the invention, the pumping devices are maintained perpendicular to the rigid base to define the predetermined orientation.

In one aspect of the invention, the system further comprises biasing means for urging the pumping mechanism toward the rigid base whereby the pumping devices are biased toward the rigid base into contact with the pumping conduit. The drive means is rigidly connected to the pumping devices such that if the pumping devices are stopped from moving, the drive means is also stopped from moving.

In one aspect of the invention, the biasing means comprises at least one tension spring attached to the device guides and the pump housing.

According to another aspect of the invention, the biasing means comprises a second tension spring attached to the device guides and the pump housing.

In a more detailed aspect of the invention, the pumping devices are slidably received in the guide device. The pumping devices are formed with a transverse slot at their proximal end for receiving the drive means which comprises a drive shaft having a plurality of cams, the cams being received in the lateral slots of the pumping devices. The drive means is rigidly coupled to the guide device so that if one or more of the pumping devices is unable to move, the drive means also cannot move.

Other features and advantages of the invention will become more apparent from the following detailed description taken in conjunction with the accompanying drawings, which illustrate by way of example, the features of the invention.

DETAILED DESCRIPTION OF THE PREFERRED EMBODIMENTS

Figure 1:
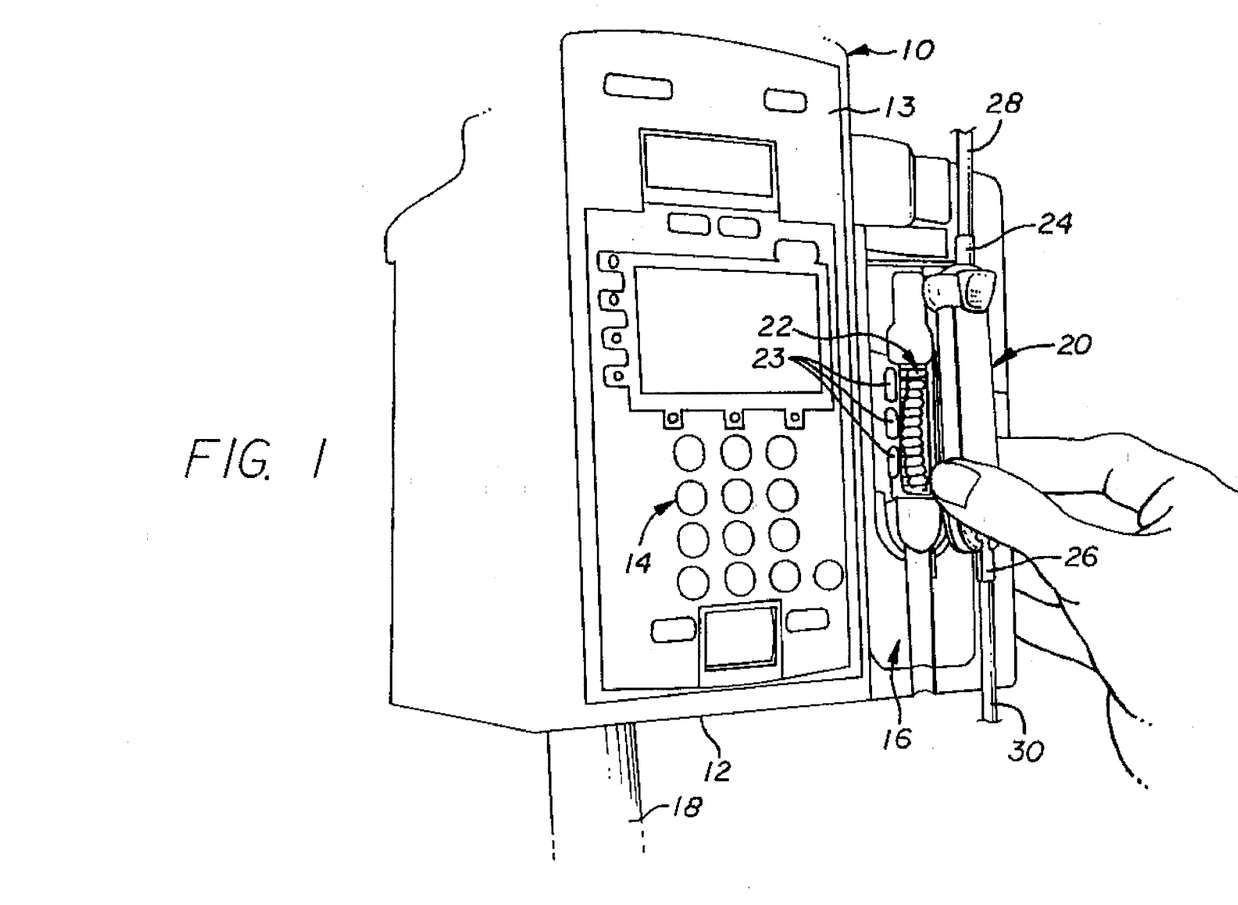
FIG. 1 is a perspective view of a fluid delivery system embodying the mounting linkage of the present invention.

In the following description, like reference numerals will be used to refer to like or corresponding elements in the different figures of the drawings. Referring now to the drawings and particularly to FIG. 1, there is shown a parenteral fluid delivery system including a mounting linkage in accordance with the principles of the present invention. The fluid delivery system may be a force limited linear peristaltic-type pump 10 and is shown for purposes of illustration.

As shown in FIG. 1, the peristaltic pump 10 has a pump housing 12 having a front panel 13 including controls and displays 14. As shown, the pump 10 is mounted on a vertical support pole 18. The pump includes a pumping unit, generally indicated at 16, that protrudes through the front panel. The pumping unit 16 is configured to mate with a detachable disposable pumping segment 20 (shown detached in FIG. 1). The pumping segment may be fixed in position against the face of the pumping unit by a plurality of clamp arms 23.

The pumping unit 16 operates on the pumping segment to pump fluid therethrough. More particularly, the pumping unit 16 has a pumping mechanism 42 (FIGS. 2 and 3) including a plurality of pumping devices 22, in this case peristaltic fingers, that sequentially occlude adjacent segments of a fluid conduit portion (not shown) of the pumping segment 20 in a wave-like motion to force fluid through the conduit.

In general, the pumping segment 20 has an inlet port 24 formed at the top end thereof and an outlet port 26 formed at the bottom end thereof, the ports in fluid communication with the fluid conduit of the pumping segment. The inlet port is connected to a length of inlet tubing 28, the opposite end of the inlet tubing in fluid communication with an elevated fluid reservoir (not shown) containing parenteral fluid. The outlet port is connected to a length of outlet tubing 30, the opposite end of the outlet tubing in fluid communication with an infusion cannula (not shown) inserted in a blood vessel of a patient for administering parenteral fluid intravenously.

Figure 6:
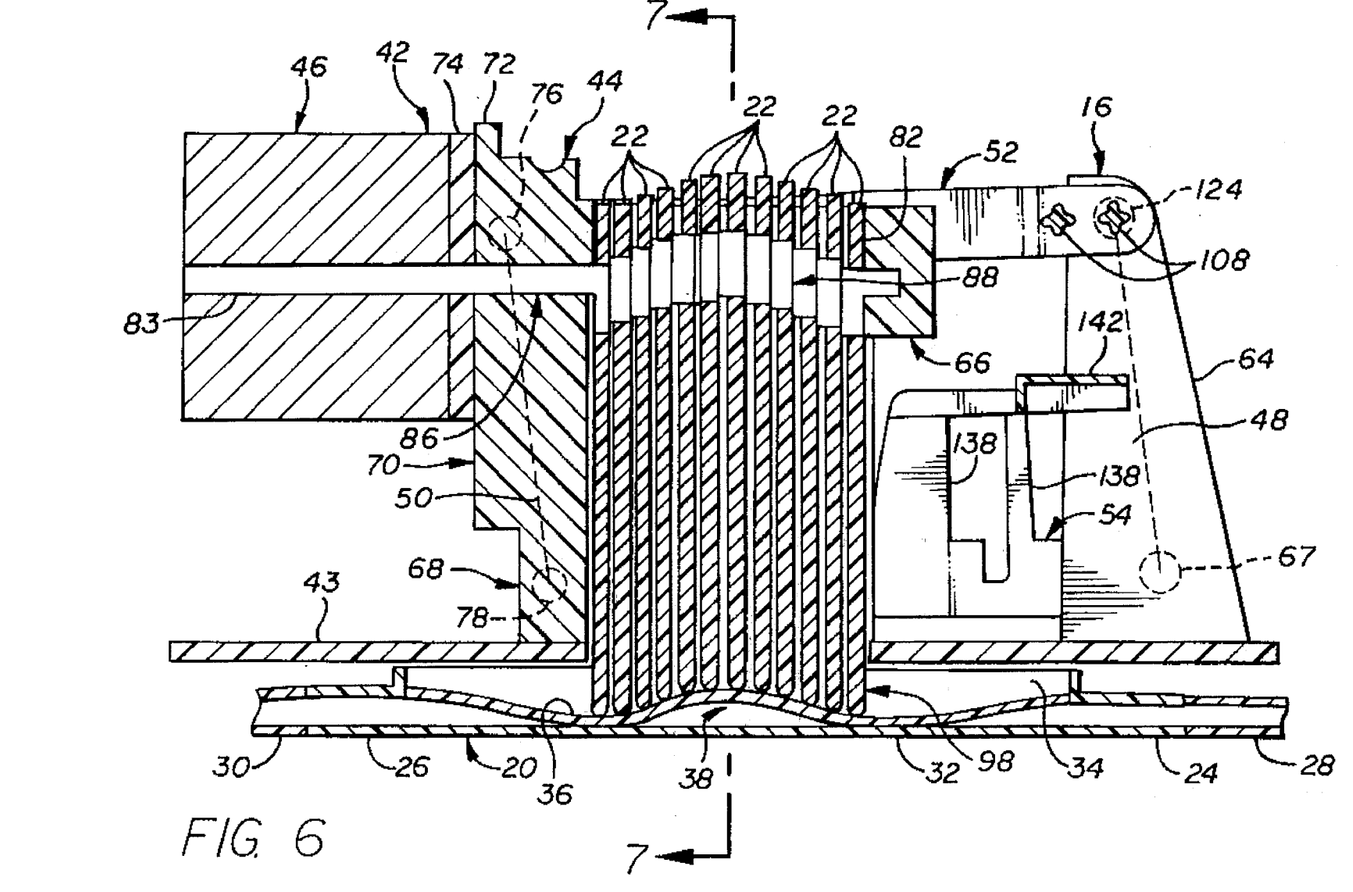
FIG. 6 is a partial sectional side view of the pumping unit shown in FIG. 4.

The pumping segment 20 is generally elongated and rectangular in shape. Referring briefly to FIG. 6, the pumping segment includes a rigid platen or base 32 having a cover with an access aperture 34 formed along the longitudinal length thereof for receiving the peristaltic fingers. An elastomeric resilient membrane 36 is disposed along the length of the aperture and parallel with the rigid base, the volume between the rigid base and membrane defining the resilient fluid conduit 38.

Figure 2:
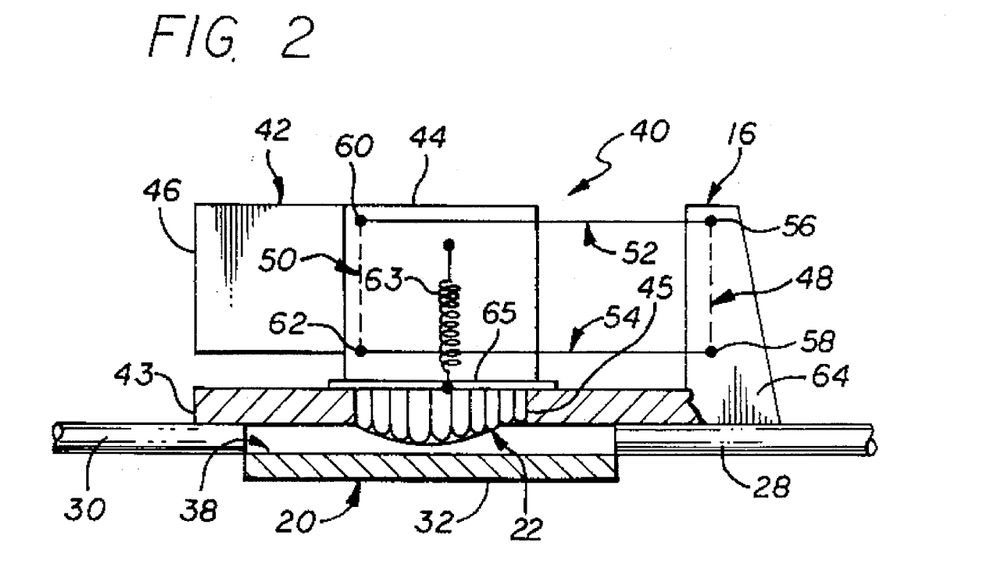
FIG. 2 is a schematic side view of a pumping unit of the fluid delivery system showing the mounting linkage mounting a pumping mechanism in a predetermined orientation relative to a rigid base of a pumping segment.
Figure 3:
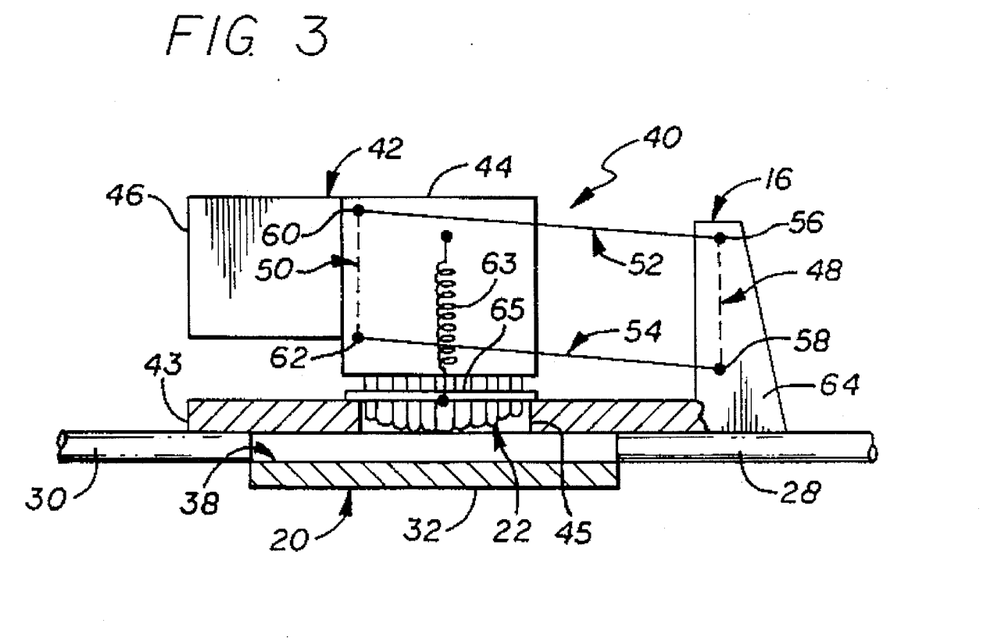
FIG. 3 is a schematic side view of the pumping unit similar to that shown in FIG. 2, but illustrating the pumping mechanism in a raised position but still with the predetermined orientation relative to the rigid base of the pumping segment in accordance with aspects of the invention.

Referring now to FIGS. 2 and 3, the pumping unit 16, shown in schematic form, includes a mounting linkage 40 for mounting the pumping mechanism 42 in a predetermined orientation relative to the rigid base 32 of the pumping segment 20 in accordance with the principles of the invention. The pumping unit has a base plate 43 including a centrally located longitudinal slot or aperture 45. The pumping mechanism 42 includes the plurality of pumping devices 22 received in a guide device 44, the plurality of pumping devices operatively connected to a step motor 46 through a cam shaft and cams (not shown) so that as the step motor rotates, the pumping devices move in a linear direction into and out of contact with the membrane 36. The step motor 46 is rigidly mounted to the guide device 44.

The mounting linkage 40 maintains the pumping devices 22 in a predetermined orientation relative to the rigid base 32 of the pumping segment. As shown in FIG. 2, the mounting linkage is configured to hold the pumping mechanism 42 so that the pumping devices 22 protrude through the longitudinal slot 45 of the pumping segment 20 and contact the membrane 36 forming a fluid conduit 38 with the rigid base 32. The fluid conduit 38 is shown in FIGS. 2 and 3 for purposes of clarity in illustration as a resilient, deformable tube placed between the rigid base 32 of the pumping segment 20 and the pumping devices 22 so that the pumping devices sequentially occlude the fluid conduit in a wave-like motion to pump fluid therethrough. The pumping segment 20 is rigidly secured relative to the base plate 43 of the pumping unit 16 by means of the clamp arms 23 (FIG. 1).

Because the pumping segment includes a rigid platen 32 that is held in rigid relation to the front of the pump, it cannot move in the event that the forces imparted on the conduit 38 exceed a limit. Thus, the pumping mechanism 42 is mounted so that it moves in relation to the rigid platen 32. When the forces against the conduit 38 reach the limit, the pumping mechanism 42 retracts into the pump to reduce those forces.

The term "link" is used to designate the arms of the mounting linkage 40. The links are connected together by joints. The mounting linkage comprises a four bar linkage designed to maintain the pumping mechanism 42 in a predetermined orientation relative to the rigid base of the pumping segment 20.

As shown, the mounting linkage 40 is in the form of a four-bar parallelogram linkage comprising a base link 48 (shown schematically by dashed lines located in a support bracket 64), a pumping mechanism link 50 (shown schematically by dashed lines located in the pumping mechanism 42 itself), and upper and lower links 52 and 54, respectively. The base link is mounted to the base plate 43 of the pumping unit 16 in a perpendicular relationship relative to the base plate. The base link has an upper and lower base link pivot joints 56 and 58 spaced apart a predetermined distance. The pumping mechanism link 50 has pumping mechanism upper and lower pivot joints 60 and 62 spaced apart the same predetermined distance as the base link pivot joints. The ends of the upper and lower link are pivotally connected to the respective upper pivot joints 56 and 60 and the lower pivot joints 58 and 62. The length between the pivotal connections of the upper and lower links are the same distance so that the interconnection of all of the links provides the parallelogram linkage.

In addition, a biasing means for biasing the pumping mechanism 42 toward the rigid base 32 of the pumping segment 20 is provided. In this case, the biasing means comprises a pair of tension springs, one of which 63 is shown. The spring 63 is connected between the pumping mechanism 42 and a spring mount 65, rigid in relation to the base plate 43. While the mounting linkage allows movement of the pumping mechanism 42 in relation to the pumping segment, the spring 63 urges the pumping mechanism 42 toward the pumping segment 20 to accomplish the pumping function. The spring force provides the force limit of the pumping devices on the conduit 38.

As illustrated in FIG. 3, the pumping mechanism 42 is in a retracted position relative to the base plate 43 and the rigid base 32 of the pumping segment 20 in opposition to the tension force of the spring 63. Although the retracted position shown is extreme in that the pumping fingers 22 are barely touching the conduit 38, this view is for clarity in understanding the operation of the mounting linkage 40. By virtue of the mounting linkage in accordance with aspects of the invention, the pumping fingers 22 remain perpendicular to the fluid conduit at all positions of the pumping mechanism 42. It should be noted that even when the pumping mechanism is in a retracted position as shown in FIG. 3, the mounting linkage 40 is still in the shape of a parallelogram with opposite sides remaining parallel. This configuration results in the pumping fingers 22 remaining perpendicular to the conduit 38 at all positions.

Although the predetermined orientation of the pumping fingers 22 in relation to the conduit 38 in FIGS. 2 and 3 is perpendicular, other orientations may be found to be desirable depending on the particular application. Other orientations may be established by changing the angle of the pumping unit 16 in the linkage so that the pumping fingers 22 are at an angle other than perpendicular to the fluid conduit 38, as will be apparent to those skilled in the art.

Figure 4:
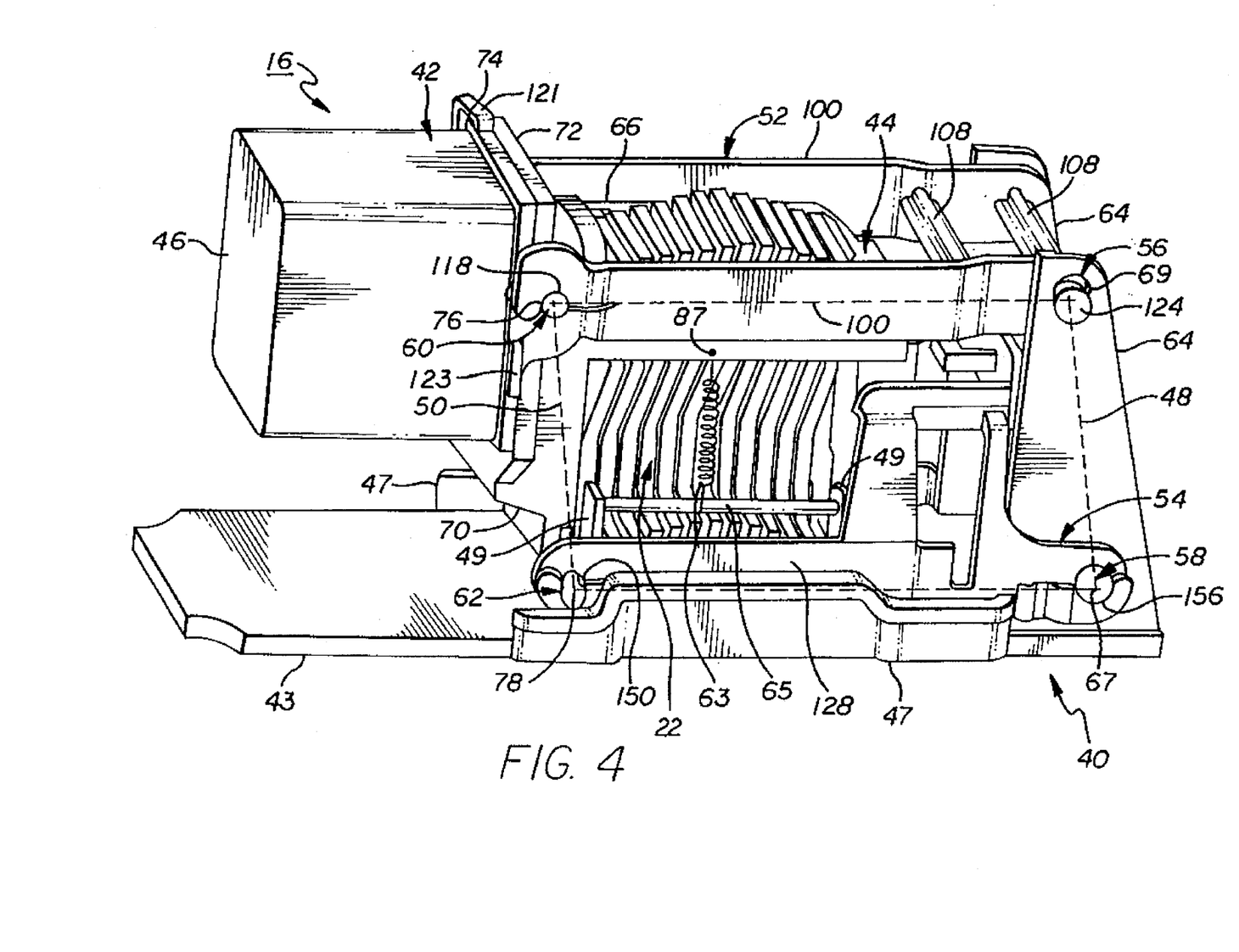
FIG. 4 is an enlarged perspective view of the pumping unit showing a four bar mounting linkage.

Referring now to FIGS. 4 through 7, the pumping unit 16 is described in more detail. With particular reference to FIG. 4, the pumping unit has a generally planar base plate 43, the lateral opposite sides of the base plate have upstanding structural support members 47 that provide structural rigidity to the pumping unit. Inwardly disposed from the respective lateral opposite sides of the rigid base 43 are a pair of longitudinally spaced apart upstanding spring support members 49 that carry the spring mount 65 therebetween for mounting a pair of tension springs 63 to the base plate (only one side shown). In addition, the rearward end of the base plate 43 is formed with two laterally spaced-apart brackets 64, the brackets defining the base link 48 shown in a dashed line drawn on the bracket. The bottom end of each of the brackets has an outwardly projecting pivot pin 67 (only one shown) aligned along the same transverse axis parallel to the base plate. The top end of each of the brackets includes a transverse pivot bore 69 (only one shown) aligned on the same central axis parallel to the axis of the pivot pins.

The base plate 43 and the brackets 64 are composed of a polymeric material, such as ABS, and are formed as one piece by an injection molding process or the like to provide a single unitary body. The ABS material is somewhat resilient so that the respective upper ends of the brackets 64 may be slightly bent during assembly, but return to their predisposed shape.

In the embodiment shown in FIGS. 4, the linkage 40 provides a parallelogram as shown in FIGS. 2 and 3, although the parallelogram in FIG. 4 is not a rectangle.

Figure 5:
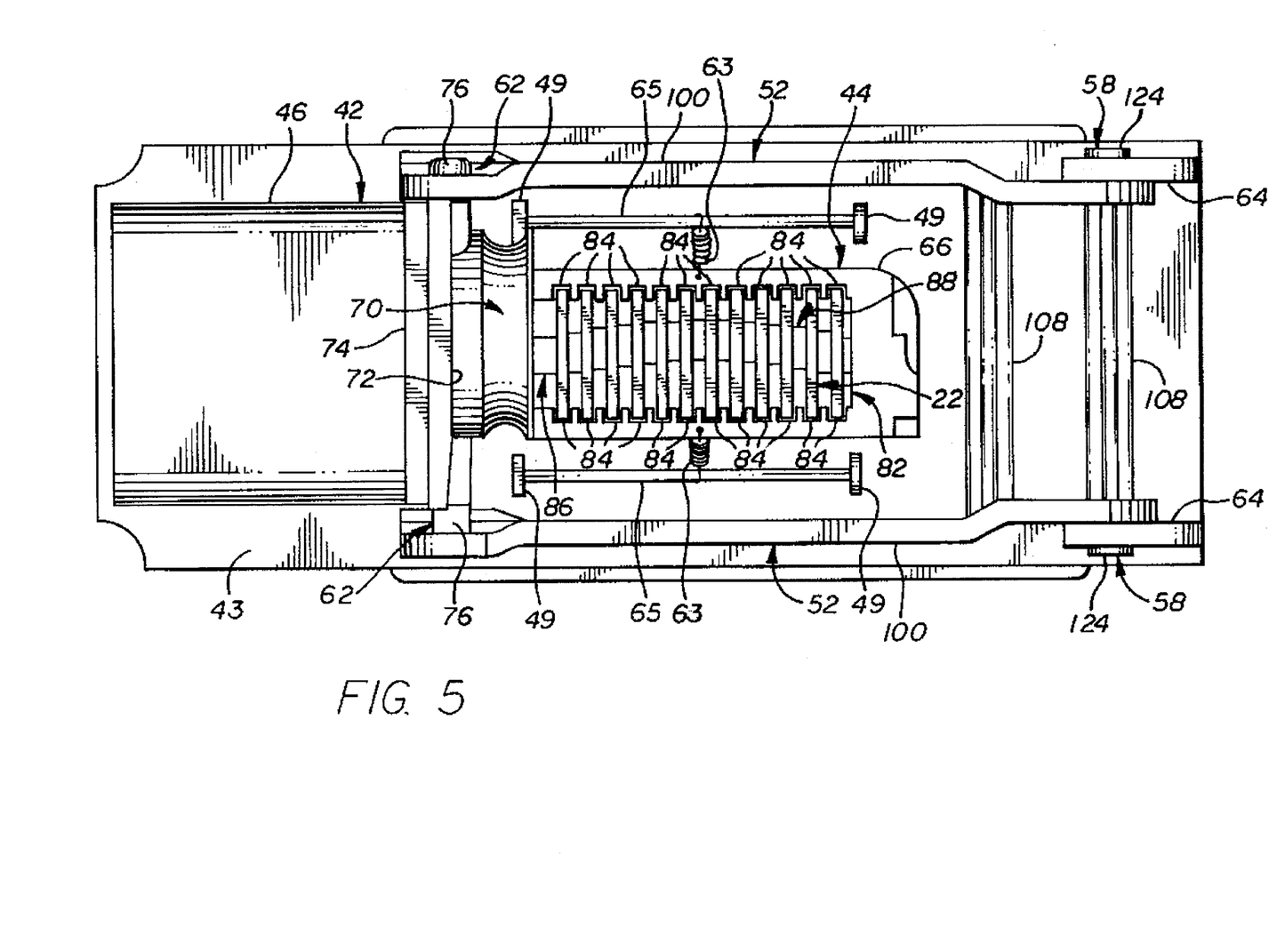
FIG. 5 is a top view of the pumping unit shown in FIG. 4.

Referring to FIGS. 5 and 6, the pumping mechanism 42 of the pumping unit 16 is described in more detail. The pumping mechanism 42 includes a step motor 46 rigidly mounted to the guide device 44. The step motor 46 includes a rotatable output shaft 83 (FIG. 6) that is coupled to a cam shaft 86 of the pumping mechanism. The cam shaft has mounted on it a plurality of adjacent cams 88, the cam lobes being angularly offset from one another. Thus the drive means in this embodiment comprises a step motor, camshaft, and cams, all of which are fixedly mounted to the guide 44.

The plurality of pumping-devices 22 are housed in the guide device 44. The guide device generally has a top 66, bottom 68, and forward ends 70. The forward end includes a mounting surface 72 to which the step motor 46 is fixedly attached by screws or the like. As shown, a shock absorbing spacer 74 is disposed between the motor and the mounting surface of the guide device. Although the spacer allows some motor movement in relation to the guide device, this movement is very limited and is only to dampen vibration. The forward end 70 of the guide device 44 has an upper pair of outwardly projecting pivot pins 76, and a lower pair of outwardly projecting pivot pins 78.

More particularly as shown in FIG. 5, the top end 66 of the guide device 44 has an elongated aperture 82, the lateral opposite sides thereof having a plurality of vertically disposed guide slots 84, extending from the top end of the guide device downwardly through vertical guide slots (not shown) formed through a like aperture 85 (FIG. 7) in the bottom end 68 of the guide device. The plurality of guide slots slidably receive the pumping devices 22.

Figure 7:
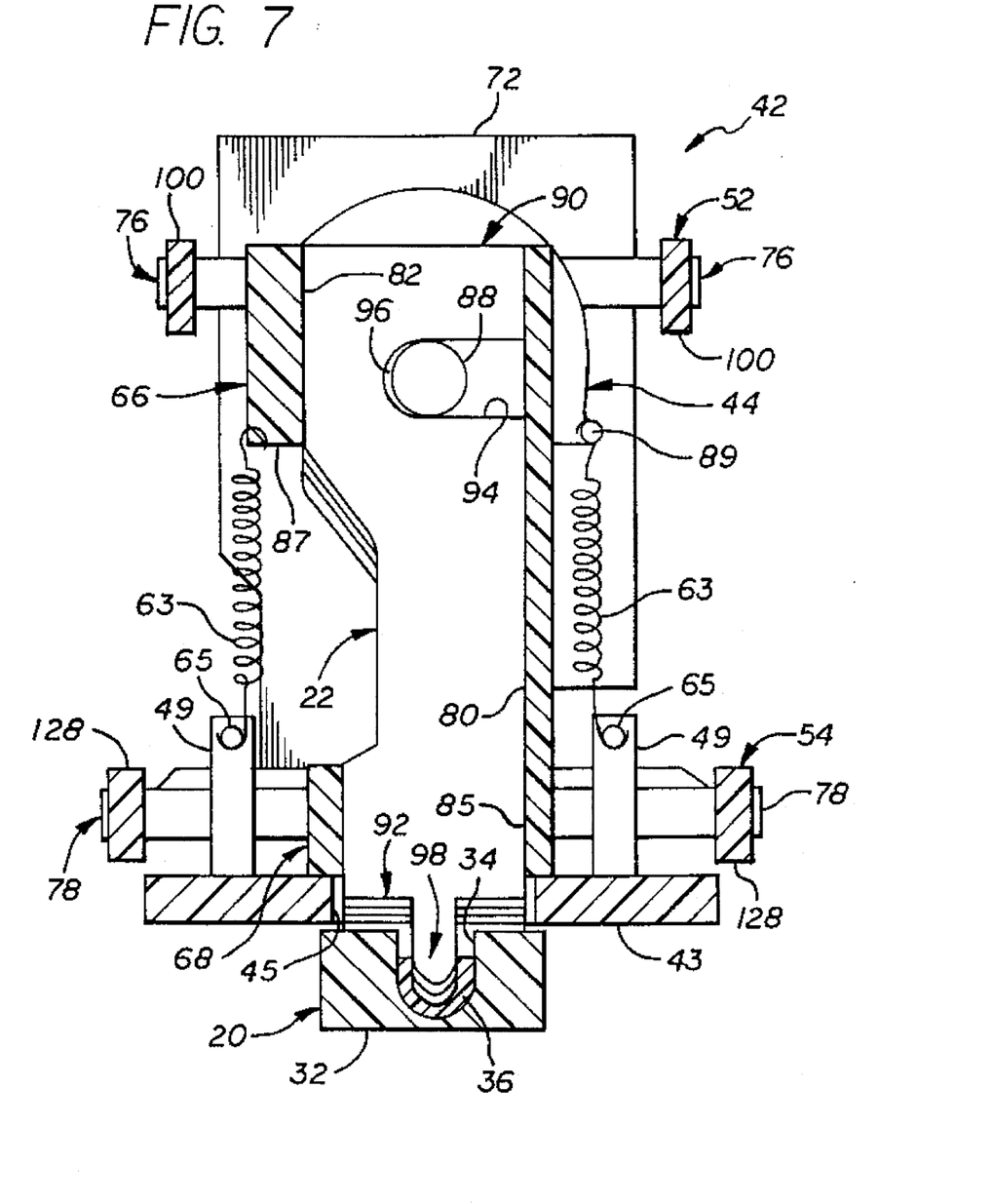
FIG. 7 is a partial sectional end view of the pumping unit taken along line 7—7 of FIG. 6 and showing the spring loading of the mechanism towards the rigid base.

With particular reference now to FIG. 7, the top end 66 of the guide device 44 is generally rectangular including a back plate 80 that extends downwardly to meet the bottom end 68 of the guide device. The front edge of the top end 66 of the guide device has a small spring retaining aperture 87 for receiving the upper hook of one of the tension springs 63. The lateral opposite top back edge of the guide block has a spring retaining loop 89 for mounting the upper hook of the other spring 63 thereon.

The guide device 44 is composed of a polymeric material, such as a rigid polyurethane, for example Isoplast made by Dow Chemical, and is formed as one piece by an injection molding process or the like to provide a single unitary body.

As shown in FIG. 7, each of the plurality of pumping devices 22 are generally elongated having a top surface 90 and bottom 92 end. The top end of each of the pumping devices has a transverse slot 94 having a generally semicircular end surface 96. The cams of the cam shaft are received in the slots of the devices in close tolerance but are free to rotate therein. Because the cam shaft is fixed relative to the guide device 44, as the cam shaft rotates, the pumping devices follow the cams sliding in the guide slots 84 (FIG. 5) in a linear reciprocating fashion. The bottom end of each of the pumping devices has a downwardly projecting finger 98 that contacts the fluid conduit for causing fluid movement through the conduit.

As described above, the pumping mechanism 42 of the pumping unit 16 is mounted by the mounting linkage 40 to the base plate 43. The components of the upper 51 and lower 54 links of the mounting linkage will be described hereinafter.

Figure 8:
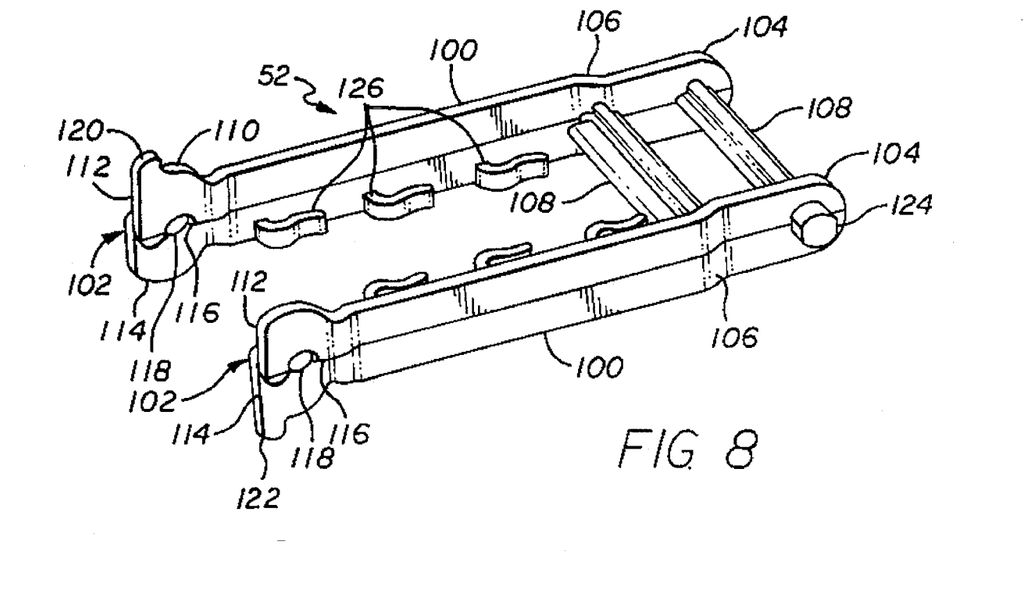
FIG. 8 is a perspective view of the upper link of the mounting linkage shown in FIG. 4.

With particular reference to FIG. 8, the upper link 52 of the mounting linkage is described in detail. Its installed position can be seen by reference to FIGS. 4, 5, and 6. The upper link has two elongated arms (links) 100, each having a forward 102 and rearward 104 end. The rearward ends of the respective arms have a slight inward transition 106. The arms are laterally spaced apart and joined together by a pair of cross members 108 at the respective rear ends thereof. In addition, the cross members 108 hold the arms in a parallel relationship to each other. The cross members are constructed having a cross section in the form of a cross.

The respective forward ends 102 of the link 100 have an enlarged head 110 split along a vertical plane taken along the center line of each respective arm to define respective top 112 and bottom 114 ends. The bottom ends 114 of the enlarged heads 110 are offset outwardly with respect to the top ends 112 of the enlarged heads. A rear fillet 116 is formed between the offset transition between the top and bottom ends. The forward extremities of the top and bottom ends are fixed together.

The respective enlarged heads 110 of the arms each include a transverse pivot bore 118 aligned along a central axis perpendicular to the arms. The enlarged heads each have a protrusion 120 and 122 respectively that assists in properly retaining the upper link to the guide device when assembled. The guide includes retainers 121 and 123 to engage the protrusions on the arms when assembled, so that the arms may rotate but will not come off the pins. To assemble the arms on the pins, the arms are rotated so that they can be slid on the pins and are then rotated into the correct operational position.

The respective rearward ends 104 of the arms each includes an outwardly projecting, generally cylindrical, pivot pin 124 aligned about a central axis perpendicular to the arms. In addition, the respective upper link arms have a plurality of inwardly and rearwardly projecting wiring clips 126 that retain wires therein when the pump unit is fully assembled.

The upper link 52 is composed of a polymeric material, such as ABS, and is formed as one piece by an injection molding process or the like to provide a single unitary body. The ABS material is somewhat resilient so that the forward ends 102 of the arms 100 may be slightly bent outwardly during assembly, but return to their predisposed shape.

Figure 9:
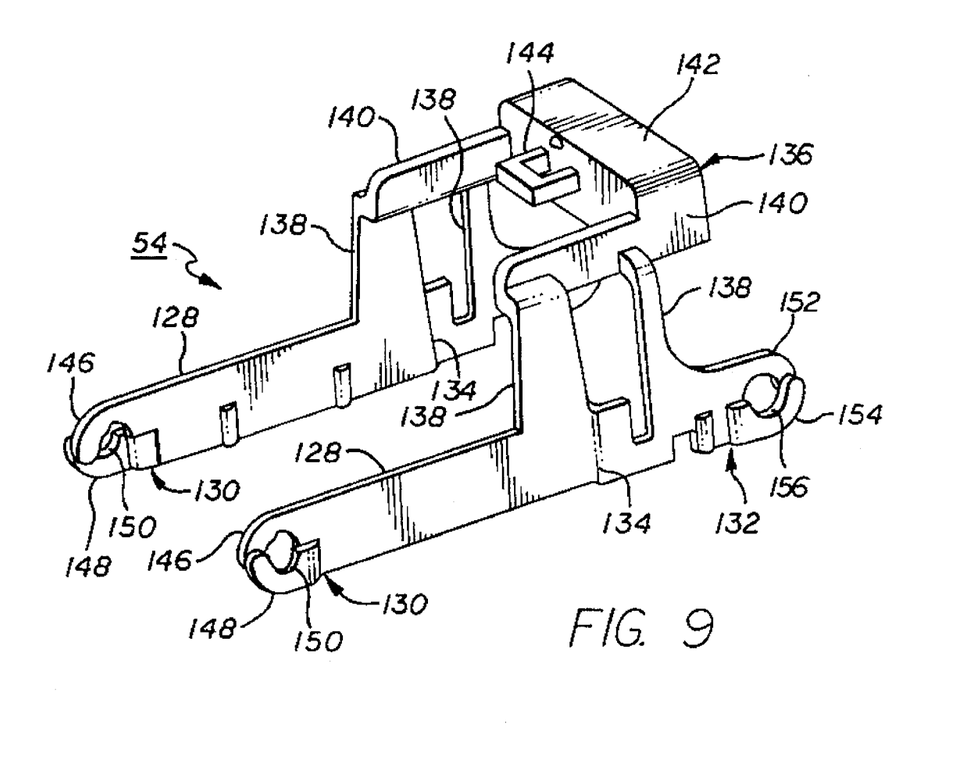
FIG. 9 is a perspective view of the lower link of the mounting linkage shown in FIG. 4.

With particular reference to FIG. 9, the lower link 54 of the mounting linkage is described in detail. Its installed position can be seen by reference to FIGS. 4 and 5. The lower link has two elongated arms or links 128 each having forward 130 and rearward 132 ends. The rearward ends of the respective arms 128 have a slight outward transition 134. The arms are spaced laterally apart and are joined at their respective rearward ends by a bridge member, generally indicated at 136. In addition, the bridge member holds the arms in a parallel relationship to each other. Each of the arms is joined to the bridge member by a pair of longitudinally spaced apart upstanding members 138, the respective top ends thereof inwardly turned to join respective longitudinal brackets 140, the respective rear ends thereof joined by a cross bar 142 of the bridge member. The cross bar has a forward projecting hook member 144 that is used to support an electrical connector (not shown in the drawings). The respective forward ends 130 of the arms 128 are split along a vertical plane to define respective top 146 and bottom 148 ends. The bottom ends 148 are offset outwardly with respect to the top ends 146. The forward extremities of the top and bottom ends are fixed together. The respective forward ends 130 of the arms include a transverse pivot bore 150 aligned along a central axis perpendicular to the arms 128. The respective rearward ends 132 of the arms 128 are split along a vertical plane to define respective rearward top 152 and bottom 154 ends. The rearward bottom ends 154 are offset outwardly with respect to the rearward top ends 152. The rearward extremities of the rearward top and bottom ends are fixed together in the molding process. The respective rearward ends of the arms each include an transverse pivot pin bore 156 aligned along the same central axis perpendicular to the arms. The raised configuration of the bridge member allows for sufficient clearance of other pump unit components when assembled, those other components not shown in the figures.

The lower link 54 is composed of a polymeric material, such as ABS, and is formed as one piece by an injection molding process or the like to provide a single unitary body. The ABS material is somewhat resilient so that the respective forward and rearward ends 130 and 132 of the lower link arms 128 may be slightly bent during assembly, but return to their predisposed shape.

Returning to FIG. 4 as well as referring also to FIGS. 8 and 9, the upper 52 and lower 54 links are shown in their assembled state. During assembly, the forward ends 130 of the lower link are slightly bent outwardly so that the lower pair of outwardly projecting pivot pins 78 of the guide block 44 are slidably received in the forward pivot bores 150 of the lower link. Likewise, the rearward ends 132 of the lower link are slightly bent outwardly so that the lower pair of outwardly projecting base link pivot pins 67 of the upstanding members 64 are slidably received in the rear pivot bores 156 of the lower link. During assembly, the forward ends 102 of the upper link 52 link are slightly bent outwardly so that the upper pair of outwardly projecting pivot pins 76 of the guide block 44 are slidably received in the forward pivot bores 118 of the upper link. The upper ends of the brackets 64 of the base link are slightly bent outwardly so that the pair of outwardly projecting upper link pivot pins 124 are slidably received in the base link pivot bores 69.

In general, when assembled, the pivotal connection between the forward end pivot bores 188 of upper link 52 and the upper projecting pivot pins 76 of the guide device 44 define the upper pumping mechanism pivot joint 60. The pivotal connection between the rearward end pivot pins 124 of the upper link and the pivot bores 69 of the base link upstanding members 64 define the base link upper pivot joint 56. The pivotal connection between the lower pivot pins 78 of the guide device and the forward end pivot bores 150 of the lower link 54 define the lower pumping mechanism pivot joint 62. The pivotal connection between the lower projection pivot pins 67 of the brackets 64 and the rearward end pivot bores 156 of lower link 54 define the lower base link pivot joint 58.

As the pumping mechanism 42 is raised relative to the base plate, the upper and lower links 52 and 54 pivot angularly about the base link pivot joints 56 and 58. The lengths of the upper and lower links 52 and 54 have been selected to be generally much longer than the length of the base link 48 and pumping mechanism link 50. Thus, as the pumping mechanism is raised, the pumping mechanism follows an arc of generally a large radius. Therefore, the longitudinal tolerances between the pumping mechanism and stationary components of the pumping unit 16 may be tighter without the concern of contact. In addition, any friction introduced at the pivot joints is minimized.

In operation, the motor is actuated to rotate the cam shaft, the cams 88 thereof driving the pumping devices 22 in a linear reciprocal manner so that the fingers 98 advance and occlude adjacent segments of the fluid conduit 38. As each finger retracts from the fluid conduit, the resiliency of the conduit and the fluid pressure therein cause the previously occluded segment of the conduit to open and allow fluid flow therethrough. The interaction and timing of the sequential cams and pumping devices cause the pumping devices to move in a wave-like peristaltic fashion.

The mounting linkage 40 of the invention assures that the guide device 44 of the pumping mechanism constrain the pumping devices in a predetermined orientation which in this embodiment is perpendicular to the rigid base.

If excessive forces are applied by a pumping device 22 on the conduit 38 against the rigid base 32, the counter force overcomes the biasing force of the springs 63 and urges the pumping devices and pumping mechanism away from the rigid base. As the pumping mechanism is urged away, the mounting linkage 40 retains the predetermined orientation of the pumping devices against the fluid conduit and rigid base so that the pumping fingers remain in their desired orientation to the fluid conduit.

In the case where parenteral fluid or other foreign agents seep into the pumping mechanism 42 and coat the surfaces between the pumping fingers 22 and the guide slots 84 of the guide device 44, such fluids may cause one or more of the pumping fingers 22 to stick to the guide device 44 and interfere with or prohibit movement of that finger. As discussed above, it is desirable in such a case that at least one of the pumping fingers continue to occlude the conduit until this "stuck" condition can be discovered and remedied. The pumping mechanism should not "back off" the conduit when one finger is stuck in a guide.

The tolerances between the transverse slots 94 of the pumping devices 22 and the cams 88 of the cam shaft 86 are such that if even one of the pumping fingers is bound, the interaction of the cam within the slot 94 prohibits the cam shaft from rotating. This effectively stalls the motor and a lack of rotation will be sensed by a rotation sensor. The pumping operation will be terminated and an alarm provided.

The drive means shown in the figures comprises a cam shaft, cams, and motor rigidly mounted to the guide device 44. However, other arrangements are possible. For example, the motor may be located separately and a flexible drive shaft coupled to the cam shaft. In this case, the drive means rigidly mounted to the guide would be the cam shaft with cams and this arrangement would likewise prevent the fingers from backing off the conduit if sticking were to occur.

While particular forms of the invention have been illustrated and described, it will be apparent that various modifications can be made to the present invention without departing from the spirit and the scope thereof.

What is claimed is:

1. A system for delivering fluid to a patient, comprising:
   a fluid conduit through which fluid is delivered to the patient;
   a pumping mechanism having a plurality of movable pumping devices guided by at least one guide device to control the direction of movement of the pumping devices and a drive means rigidly mounted to the guide device and operative on the pumping devices to move the pumping devices in the guide device through a predetermined range of motion;
   a rigid base mounted so as to position the fluid conduit between itself and the pumping mechanism; and
   a mounting linkage connected to the pumping mechanism to mount the pumping mechanism in a predetermined orientation relative to the rigid base and in relation to the fluid conduit so that the pumping devices move into and out of contact with the fluid conduit to move fluid through the conduit, the linkage configured to allow movement of the pumping mechanism relative to the rigid base, but to constrain such movement to the predetermined orientation.

2. The system of claim 1, wherein the mounting linkage comprises a plurality of links pivotally interconnected at the ends thereof wherein one of such links, defined as a base link, is fixed in relationship to the rigid base.

3. The system of claim 2, wherein another one of the links comprises the pumping mechanism to define a pumping mechanism link, the pumping mechanism link connected by at least one link to the base link.

4. The system of claim 3, wherein the mounting linkage comprises a four-bar linkage, the base link and pumping mechanism link having first and second ends, the respective first ends pivotally connected to the ends of a third link and the respective second ends pivotally connected to the ends of a fourth link.

5. The system of claim 1, wherein the pumping devices are perpendicular to the fluid conduit to define the predetermined orientation.

6. The system of claim 1, wherein the system further comprises biasing means for urging the pumping mechanism toward the rigid base whereby the pumping devices are biased toward the rigid base into contact with the fluid conduit.

7. The system of claim 6, wherein the biasing means comprises at least one spring connected to the pumping mechanism and a housing mounting the rigid base.

8. The system of claim 7, wherein the at least one spring is a tension spring.

9. The system of claim 6, wherein the biasing means comprises a second spring connected to the pumping mechanism and the housing mounting the rigid base.

10. The system of claim 9, wherein the second spring is a tension spring.

11. The system of claim 1, wherein the pumping devices are slidably received in the guide device.

12. The system of claim 11, wherein each of the plurality of pumping devices has a transverse slot at its proximal end for receiving the drive means.

13. The system of claim 12, wherein the drive means is coupled to a drive motor and the drive means comprises a drive shaft having a plurality of cams, the cams being received in the lateral slots of the pumping devices so that if the pumping devices are unable to move, the drive means cannot move.

14. The system of claim 13, wherein the drive motor is rigidly mounted to the guide device.

15. A system for delivering fluid to a patient, comprising:
   a fluid conduit through which fluid is delivered to the patient;
   a pumping mechanism having a plurality of movable pumping devices guided by at least one guide device to control the direction of movement of the pumping devices and a drive means rigidly mounted to the guide device and operative on the pumping devices to move the pumping devices in the guide device through a predetermined range of motion, wherein the drive means is coupled to the pumping devices so that if the pumping devices are unable to move, the drive means cannot move;
   a rigid base mounted so as to position the fluid conduit between itself and the pumping mechanism;
   a mounting linkage connected to the pumping mechanism to mount the pumping mechanism in a predetermined orientation relative to the rigid base and in relation to the fluid conduit so that the pumping devices move into and out of contact with the fluid conduit to move fluid through the conduit, the linkage configured to allow movement of the pumping mechanism relative to the rigid base; and
   biasing means for urging the pumping mechanism toward the rigid base whereby the pumping devices are biased toward the rigid base into contact with the fluid conduit.

16. The system of claim 15, wherein the biasing means comprises at least one spring connected to the pumping mechanism and a housing mounting the rigid base.

17. The system of claim 16 wherein the at least one spring is a tension spring.

18. The system of claim 16 wherein the biasing means comprises a second spring connected to the pumping mechanism and the housing mounting the rigid base.

19. The system of claim 18 wherein the second spring is a tension spring.

20. The system of claim 15 wherein the pumping devices are slidably received in the guide device.

21. The system of claim 15 wherein each of the plurality of pumping devices has a transverse slot at its proximal end for receiving the drive means.

22. The system of claim 21 wherein the drive means is coupled to a drive motor and the drive means comprises a drive shaft having a plurality of cams, the cams being received in the lateral slots of the pumping devices so that if the pumping devices are unable to move, the drive means cannot move.

23. The system of claim 22 wherein the drive motor is rigidly mounted to the guide device.

* * * * *